(12) United States Patent
Doerr et al.

(10) Patent No.: US 10,285,614 B2
(45) Date of Patent: May 14, 2019

(54) IMPLANTABLE CARDIAC SYSTEM HAVING AN R-SPIKE AMPLIFIER

(71) Applicant: BIOTRONIK SE & Co. KG, Berlin (DE)

(72) Inventors: Thomas Doerr, Berlin (DE); Dirk Muessig, West Linn, OR (US)

(73) Assignee: BIOTRONIK SE & Co. KG, Berlin (DE)

(*) Notice: Subject to any disclaimer, the term of this patent is extended or adjusted under 35 U.S.C. 154(b) by 133 days.

(21) Appl. No.: 15/642,807

(22) Filed: Jul. 6, 2017

(65) Prior Publication Data

US 2018/0020940 A1 Jan. 25, 2018

Related U.S. Application Data

(60) Provisional application No. 62/363,867, filed on Jul. 19, 2016.

(51) Int. Cl.

| *A61B 5/04* | (2006.01) |
|---|---|
| *A61B 5/0456* | (2006.01) |
| *A61N 1/375* | (2006.01) |
| *A61N 1/365* | (2006.01) |
| *A61N 1/39* | (2006.01) |
| *A61N 1/372* | (2006.01) |

(52) U.S. Cl.
CPC ........ *A61B 5/0456* (2013.01); *A61B 5/04012* (2013.01); *A61N 1/36514* (2013.01); *A61N 1/3756* (2013.01); *A61N 1/37288* (2013.01); *A61N 1/37512* (2017.08); *A61N 1/3925* (2013.01); *A61N 1/3987* (2013.01); *A61N 1/39622* (2017.08)

(58) Field of Classification Search
None
See application file for complete search history.

(56) References Cited

U.S. PATENT DOCUMENTS

| 2010/0030289 A1* | 2/2010 | Casavant | A61N 1/3622 607/4 |
|---|---|---|---|
| 2013/0096449 A1* | 4/2013 | Patel | A61B 5/046 600/516 |
| 2015/0297905 A1 | 10/2015 | Greenhut et al. | |

* cited by examiner

*Primary Examiner* — Ankit D Tejani
(74) *Attorney, Agent, or Firm* — Buchanan Intersoll & Rooney PC

(57) ABSTRACT

An implantable cardiac system that includes an implantable cardiac pacemaker or leadless pacemaker (iLP) and a second device such as a subcutaneous implantable cardioverter-defibrillator (S-ICD). The pacemaker includes an R-spike amplifier that amplifies stimulated ventricle excitations or R-waves to increase R-wave to T-wave signal to noise ratio and to improve indirect detection of ventricular rhythm classification by the S-ICD. The S-ICD includes an electrode line for defibrillation, a sensing unit and a stimulation detection unit. The S-ICD records a subcutaneous electrocardiogram between shock electrode poles and provides potentially life-saving therapy based thereon. The system significantly increases the specificity and sensitivity of an S-ICD in combination with an implanted cardiac pacemaker or iLP having an R-spike amplifier.

20 Claims, 5 Drawing Sheets

IMPLANTABLE CARDIAC SYSTEM HAVING AN R-SPIKE AMPLIFIER

CROSS-REFERENCE TO RELATED APPLICATIONS

This patent application claims the benefit of U.S. Provisional Patent Application No. 62/363,867, filed on Jul. 19, 2016, which is hereby incorporated by reference in its entirety.

BACKGROUND OF THE INVENTION

Field of the Invention

Embodiments of the present invention generally relate to an implantable cardiac system including an implantable cardiac pacemaker that includes an R-spike amplifier that amplifies sensed and stimulated ventricle excitations, in general to increase R-wave to T-wave signal to noise ratio and to improve indirect detection of ventricular rhythm classification by another device, such as, for example, a subcutaneous implantable cardioverter-defibrillator (S-ICD).

Description of the Related Art

Currently available subcutaneous implantable cardioverter-defibrillator (S-ICD) solutions have disadvantages compared with conventional implantable cardioverter-defibrillator (ICD) systems. For example, an S-ICD has no capability for pacing the heart. Another disadvantage is size, wherein current S-ICD apparatus are large based on increased power requirements and battery size required for distal defibrillation, e.g., from outside the thoracic cavity. Subcutaneous electrocardiogram (ECG) signal recording has been found, in particular, to be problematic and susceptible to faults. For this reason, it is necessary when implanting this S-ICD that the available ECG signal recordings are checked by means of a template prior to implantation, and implantation is possible only when the signals corresponds to the predefined form, in particular, signal size and R-wave to T-wave ratio. The necessary detection times for a sufficiently specific ventricular fibrillation detection are also relatively long and can lead, along with interfering signals on the body surface, to a considerable therapy delay or absence of the life-supporting therapy.

One such system described in United States Patent Application Publication No. 2015/0297905, entitled "SYSTEMS AND METHODS FOR LEADLESS PACING AND SHOCK THERAPY" shows a combination of an S-ICD and a leadless pacemaker and teaches that the S-ICD may be implanted external to a rib cage of a patient without any leads implanted within the rib cage or within the vasculature and may detect tachyarrhythmias and/or deliver anti-tachyarrhythmia shock therapy. The publication also teaches that the pacemaker may be implanted within a chamber of the heart and include one or more electrodes for monitoring cardiac signals and/or delivering anti-tachycardia pacing therapy. The publication also teaches that the S-ICD and pacemaker may communicate with one another with a variety of different communication protocols such as radiofrequency telemetry, inductive coupling, or electrical signals from implanted electrodes.

The present invention is directed toward overcoming one or more of the above-mentioned problems.

Thus, in view of the limitations of the known art, there is a need for an implantable cardiac system having an R-spike amplifier.

BRIEF SUMMARY OF THE INVENTION

One or more embodiments of the present invention include an implantable cardiac system that includes an implantable cardiac pacemaker with an R-spike amplifier that enhances or otherwise amplifies at least a portion of an R-wave to increase an R-wave to T-wave signal to noise ratio associated with electrical signals of a heart. The implantable cardiac pacemaker may include leads that traverse the heart or may be leadless (iLP), for example, that may be implanted in a ventricle of a heart, including the right ventricle. The system generally includes another device that takes advantage of the increased amplitude of the R-wave, such as, for example, a subcutaneous implantable cardioverter-defibrillator (S-ICD) communicatively coupled to the implantable cardiac pacemaker. For example, in one or more embodiments, sub-threshold stimulation is performed by the implantable cardiac system in the event of detection of natural ventricular activity to assist the ventricular rhythm sensing function of the S-ICD. The amplified R-wave or R-spike for paced events also increases the R-wave to T-wave signal to noise ratio. Thus, embodiments of the present invention enable reliable S-ICD rhythm classification even when the subcutaneous ECG is temporarily or permanently disturbed or the signal conditions are unsuitable in principle for S-ICD sensing and significantly improve the R-spike detection of in the S-ICD.

Specifically, embodiments of the implantable cardiac system having an R-spike amplifier include an implantable cardiac pacemaker that includes an electrode, an electrical signal processor coupled with the electrode, wherein the electrical signal processor is configured to detect a ventricle excitation that is either a sensed ventricular excitation or a stimulated ventricular excitation of a heart. The R-spike amplifier is generally coupled with the electrical signal processor, wherein the R-spike amplifier is configured to amplify the ventricle excitation to create an amplified R-wave and output the amplified R-wave or R-spike and increase an R-wave to T-wave signal to noise ratio associated with the heart.

Embodiments of the present invention may output the amplified R-wave during a time period that is shorter in time duration than the ventricle excitation or longer in the time duration than the ventricle excitation. As long as the amplitude of the amplified R-wave is increased without increasing the amplitude of the subsequent T-wave, or at least as long as the ratio of the R-wave amplitude to the subsequent T-wave is increased, then embodiments of the inventive system enable a second device such as, for example, an S-ICD to significantly improve the sensing function of the S-ICD. Thus, the inventive system reduces detection times for ventricular fibrillation to minimize therapy delay and enable the S-ICD to provide life-supporting therapy.

For example, in one or more embodiments, the amplified R-wave that is output from the implantable cardiac pacemaker ends before an initial increase in a subsequent T-wave. Thus, the portion of the electrical signal associated with the heart that is associated with the R-wave has a larger amplitude than un-amplified R-wave, while the remaining portion of the electrical signal remains unamplified.

In one or more embodiments, the implantable cardiac pacemaker is further configured to record a subcutaneous electrocardiogram (ECG) as a time course of electrical activity of the heart. In this embodiment, the R-spike amplifier is configured to amplify the ventricle excitation during a fraction of time of the time course of the electrical activity of the heart before a subsequent T-wave and output the amplified R-wave. In this embodiment, the R-wave may have a different duration or starting or ending point in time with respect to the amplified R-wave.

In one or more embodiments, the implantable cardiac pacemaker is a leadless cardiac pacemaker (iLP) configured to be implanted in a ventricle of the heart. Any other type of cardiac pacemaker may be utilized in the inventive system so long as the amplitude of R-wave is altered with respect to another portion of the subcutaneous electrocardiogram.

In one or more embodiments, the implantable cardiac pacemaker is further configured to deliver a sub-threshold stimulation pulse after the ventricle excitation is sensed. In this manner, the amplified R-wave does not cause capture or otherwise interfere with the heart.

In one or more embodiments, the implantable cardiac pacemaker is further configured to deliver a stimulation pulse after the ventricle excitation is sensed based on a heart rate of the heart, such that when the heart rate is below a first predefined threshold value, the stimulation pulse is delivered as a supra-threshold stimulation pulse, and when the heart rate is above a second predefined threshold value, the stimulation pulse is delivered as a sub-threshold stimulation pulse. Embodiments may also inhibit delivery of the stimulation pulses after the ventricle excitation is sensed based on the heart rate of the heart, such that when the heart rate lies above the first predefined threshold value and below the second predefined threshold value, the stimulation pulse is not delivered.

Embodiments of the implantable cardiac pacemaker further include a stimulation electrode and a stimulation unit coupled to the stimulation electrode. In these embodiments, the pacemaker may operate in any manner and may stimulate any chamber of the heart. In one or more embodiments, the implantable cardiac pacemaker further comprises a sensing unit coupled to the electrode, and a control unit coupled to the sensing unit, the stimulation electrode and the electrode. Sensing may take place in any chamber of the heart.

In one or more embodiments of the present invention, the sensing unit is coupled to the electrical signal processor and is configured to transmit an indication to the control unit that indicates natural ventricular activity of the heart. In one or more embodiments, the implantable cardiac pacemaker is operated in a VVT operating mode.

Embodiments of the implantable cardiac pacemaker further comprises an elevation unit, wherein the elevation unit is controlled by the control unit and is configured to deliver an electrical signal increase that corresponds to a frequency spectrum of the electrical activity of the heart when the control unit receives the indication that indicates the natural ventricular activity or when a stimulation pulse is delivered via the stimulation unit. In one or more embodiments, the electrical signal increase comprises an increase of the R-wave, e.g., increase in amplitude, in the electrical activity of the heart to form the amplified R-wave or R-spike.

In one or more embodiments, the inventive system includes a second device such as, for example, a subcutaneous implantable cardioverter-defibrillator (S-ICD). The S-ICD is communicatively coupled to the implantable cardiac pacemaker, for example, wirelessly, wherein the subcutaneous implantable cardioverter-defibrillator comprises an electrode line that comprises two shock electrode poles, wherein the subcutaneous implantable cardioverter-defibrillator is configured to record a second subcutaneous electrocardiogram (ECG) between the two shock electrode poles. The S-ICD may also include a stimulation detection unit coupled with the electrode line wherein the stimulation detection unit is configured to identify and detect a characteristic feature in the subcutaneous electrocardiogram. The S-ICD may also include a sensing unit coupled with the stimulation detection unit wherein the sensing unit is configured obtain the characteristic feature in the subcutaneous electrocardiogram and sense the amplified R-wave based on the increase in the R-wave to T-wave signal to noise ratio associated with the heart.

At least one embodiment of the electrical signal processor in the implantable cardiac pacemaker is further configured to amplify the ventricular tachyarrhythmia that is detected, such that the second subcutaneous electrocardiogram detected by the S-ICD further comprises the ventricular tachyarrhythmia as amplified by the implantable cardiac pacemaker.

At least one embodiment of the implantable cardiac pacemaker further comprises a pacemaker stimulation detection unit coupled to the electrical signal processor, wherein the pacemaker stimulation detection unit is configured to detect a stimulation from the subcutaneous implantable cardioverter-defibrillator and classify the stimulation as effective or ineffective, and wherein the R-spike amplifier is further configured to amplify stimulated ventricle excitation only when the pacemaker stimulation detection unit classifies the stimulation as effective.

One or more embodiments of the implantable cardiac pacemaker further comprises a classification unit configured to detect and classify ventricular tachyarrhythmia from more than one the ventricle excitation, such that the implantable cardiac pacemaker is further configured to deliver an antitachycardia stimulation when the ventricular tachyarrhythmia is detected, and wherein the subcutaneous implantable cardioverter-defibrillator is further configured to trigger a defibrillation shock when a rate of the antitachycardia stimulation exceeds a predefined ventricular tachyarrhythmia threshold value.

In one or more embodiments, the subcutaneous implantable cardioverter-defibrillator further comprises a classification unit configured to detect and classify ventricular tachyarrhythmia or tachycardia and ventricular fibrillation.

In one or more embodiments, the sensing unit of the subcutaneous implantable cardioverter-defibrillator is further configured to detect the amplified R-wave and calculate an R-wave to T-wave signal to noise ratio to minimize T-wave over-sensing. In at least one of these embodiments, the subcutaneous implantable cardioverter-defibrillator is further configured to send a message to the implantable cardiac pacemaker to alter an amplification factor utilized by the R-spike amplifier to create the amplified R-wave based on the R-wave to T-wave signal to noise ratio.

Further embodiments, features, aspects, objects, advantages, and possible applications of the present invention could be learned from the following description, in combination with the Figures, and the appended claims.

BRIEF DESCRIPTION OF THE DRAWINGS

The above and other aspects, features and advantages of at least one embodiment of the present invention will be more apparent from the following more particular description thereof, presented in conjunction with the following drawings, wherein.

DETAILED DESCRIPTION OF THE INVENTION

The following description is of the best mode presently contemplated for carrying out at least one embodiment of the present invention. This description is not to be taken in a limiting sense, but is made merely for the purpose of describing the general principles of the present invention. The scope of the present invention should be determined with reference to the claims.

Figure 1:
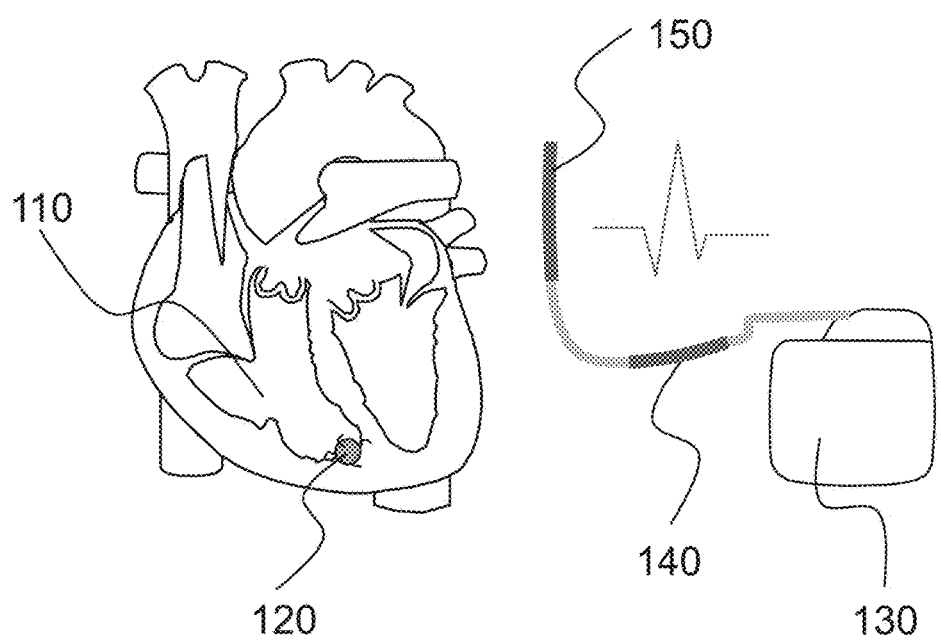
FIG. 1 shows an overall depiction of the implantable cardiac system with an implantable cardiac pacemaker and a subcutaneous implantable cardioverter-defibrillator.

FIG. 1 shows an overall depiction of the implantable cardiac system with an implantable cardiac pacemaker and a subcutaneous implantable cardioverter-defibrillator. One or more embodiments of the present invention include an implantable cardiac system that includes an implantable cardiac pacemaker 120 with an R-spike amplifier that enhances or otherwise amplifies at least a portion of an R-wave to increase an R-wave to T-wave signal to noise ratio associated with electrical signals in a chamber of heart 110. The implantable cardiac pacemaker may include leads that traverse the heart or may be leadless (iLP), for example, that may be implanted in a ventricle of a heart, including the right ventricle. The system generally includes another device that takes advantage of the increased amplitude of the R-wave, such as, for example, a subcutaneous implantable cardioverter-defibrillator (S-ICD) 130 communicatively coupled to the implantable cardiac pacemaker. As shown, S-ICD 130 is connected to an electrode line that is implanted subcutaneously, which has two shock electrode poles 140, 150 to record a subcutaneous ECG and the delivered pacemaker pulses from the implantable cardiac pacemaker. The subcutaneous ECG is recorded for ventricular rhythm classification and utilized for therapy decisions by the S-ICD.

In one or more embodiments, sub-threshold stimulation is performed by the implantable cardiac system in the event of detection of natural ventricular activity to assist the ventricular rhythm sensing function of the S-ICD. The amplified R-wave or R-spike for paced events increases the R-wave to T-wave signal to noise ratio. Thus, embodiments of the present invention enable reliable S-ICD rhythm classification even when the subcutaneous ECG is temporarily or permanently disturbed or the signal conditions are unsuitable in principle for S-ICD sensing and significantly improve the R-spike detection of in the S-ICD.

Figure 2A:
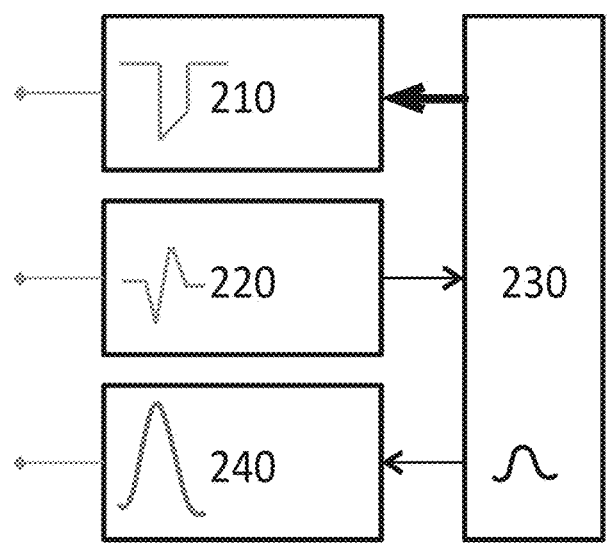
FIG. 2A shows a block diagram of components of the implantable cardiac pacemaker.

FIG. 2A shows a block diagram of components of the implantable cardiac pacemaker 120. Implantable cardiac pacemaker 120 includes a stimulation unit 210 connected to an electrode pole or poles for example stimulation electrode poles for antibradycardia and optionally antitachycardia stimulation of the heart. To sense the natural cardiac activity, a sensing unit 220 is connected to the electrode poles and signals from the intracardially recorded ECG associated with natural ventricular activity are sent to the central control unit 230. Embodiments of the present invention include ECG super-elevation unit 240, which is controlled by the control unit 230 and delivers, via the connected electrode poles, an electric signal increase corresponding to the R-wave whenever natural cardiac activity has been signalled or a stimulation pulse has been delivered, such that the amplified R-wave or R-spike in the subcutaneously recorded ECG of an S-ICD is increased compared with the other signal components or time periods within a heartbeat, for example.

Figure 2B:
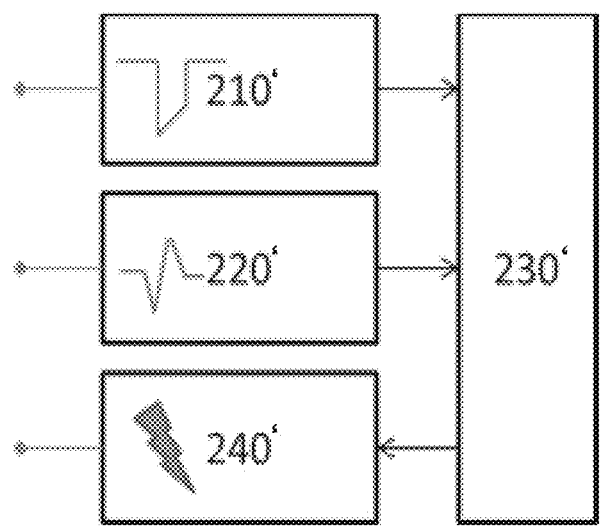
FIG. 2B shows a block diagram of components of the subcutaneous implantable cardioverter-defibrillator.

FIG. 2B shows a block diagram of components of the subcutaneous implantable cardioverter-defibrillator S-ICD 130. Embodiments of the S-ICD may include first sensing unit 210', designed to isolate the characteristic signal content of the pacemaker pulse mapped to the subcutaneous electrodes from the rest of the signal content and to sense the presence of a pacemaker pulse. Embodiments of the S-ICD may also include a second sensing unit 220' to sense and identify amplified R-waves or R-spikes from the recorded subcutaneous ECG and to control unit 230'. Specifically, both sensing units are connected to a control unit 230', which provides the actual sensing of the cardiac activity from the signalling of pacemaker pulses and R-spikes and from this classifies the interval lengths for example. If the cardiac activity is considered to be tachycardial, a defibrillation therapy is initiated via the therapy unit 240' via the control unit once an appropriate tachycardia duration or interval number has been reached, for example.

The control unit 230' may be configured, for example, to classify an R-wave only when, at the same time, a pacemaker pulse has been sensed. It is thus possible to prevent a T-wave from being incorrectly classified as ventricular activity. In the case of temporarily unsuitable ECG signals, for example, when amplitudes are beneath a threshold, or in the case of noise, etc., the control unit may control the rhythm classification through evaluation of the pacemaker pulses, e.g., as amplified by the implantable cardiac pacemaker, such that there is no delay or total inhibition of the ICD therapy due to unsuitable ECG signals.

Figure 3A:
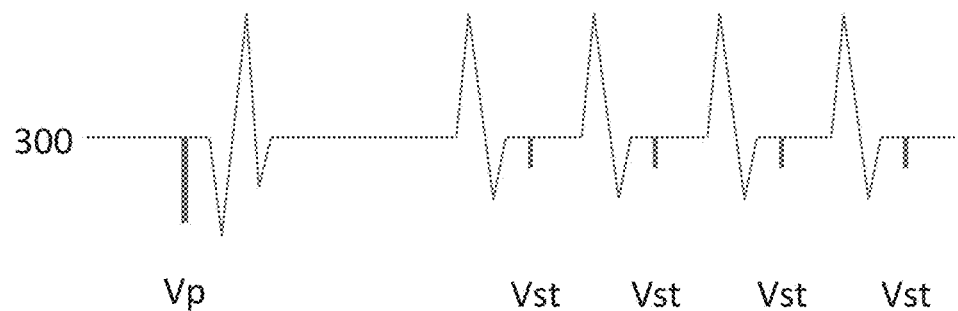
FIG. 3A shows a diagram of supra-threshold VVT stimulation and sub-threshold VVT stimulation.

FIG. 3A shows a diagram an electrocardiogram signal 300 with supra-threshold VVT stimulation and sub-threshold VVT stimulation according to one or more embodiments of the present invention. In this embodiment, the VVT pacemaker delivers a supra-threshold stimulation pulse or paced pulse Vp only when the need for cardiac stimulation is indicated by the pacemaker timer. In this case, the corresponding R-wave follows after the stimulation of the heart Vp. If natural cardiac activity is identified within the ventricular beat-to-beat interval, the pacemaker delivers a sub-threshold pulse Vst, and therefore considerably reduced stimulation energy. In this case, the intrinsic R-wave is before the stimulation Vst. The amplitude of the sub-threshold pulse may be adjusted such that the pulse is reliably identified by the S-ICD. Utilizing sub-threshold pulses to augment the subcutaneous ECG considerably reduces the power demand of the VVT stimulation.

Figure 3B:
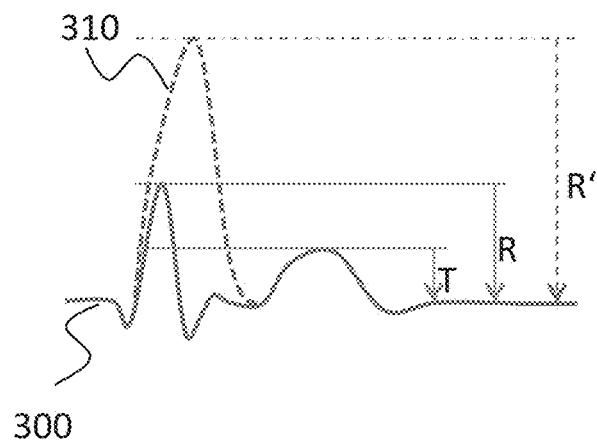
FIG. 3B shows a diagram of an electrocardiogram signal recorded by the subcutaneous implantable cardioverter-defibrillator and an enhanced R-wave signal.

FIG. 3B shows a diagram of the electrocardiogram signal 300 recorded by the subcutaneous implantable cardioverter-defibrillator and an enhanced R-wave signal. As shown in this exemplary diagram, a pronounced T-wave can be seen subsequent in time with respect to the R-wave. The signal ratio of R to T is unsuitable as shown with respect to the un-amplified R-wave, or first peak on the left of the diagram, for reliable detection of cardiac activity by an S-ICD, since the T-wave will most likely be sensed as cardiac activity or as an R-wave, which is known as T-wave over-sensing.

The R-wave super-elevation that results in amplified R-wave or R-spike 310 as output by the implantable cardiac pacemaker 120 considerably improves the R-wave to T-wave signal to noise ratio and thus enables a significant improvement of the sensing quality of the S-ICD. Embodiments of the present invention may be utilized with existing unmodified S-ICD's by implementing the R-spike mechanisms in implantable cardiac pacemaker 120.

Figure 4:
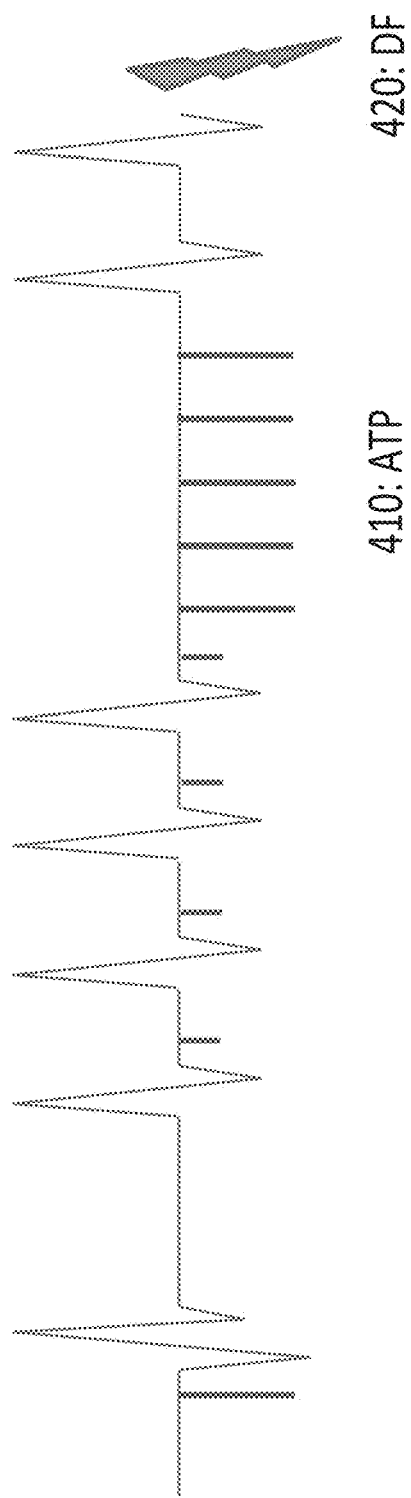
FIG. 4 shows an extended stimulation sequence with antitachycardia stimulation.

FIG. 4 shows an extended stimulation sequence with antitachycardia stimulation. As shown, the implantable cardiac pacemaker 120, for example, a VVT pacemaker, is additionally able to deliver an antitachycardia stimulation (ATP) 410 so as to deliver a painless and power-saving therapy in the case of regular ventricular tachycardia. If the tachycardia frequency exceeds a threshold value, the ATP frequency coupled to this can lead to a triggering of a defibrillation therapy 420 in the S-ICD and can thus effectively combine the functions of ATP and defibrillation.

Figure 5:
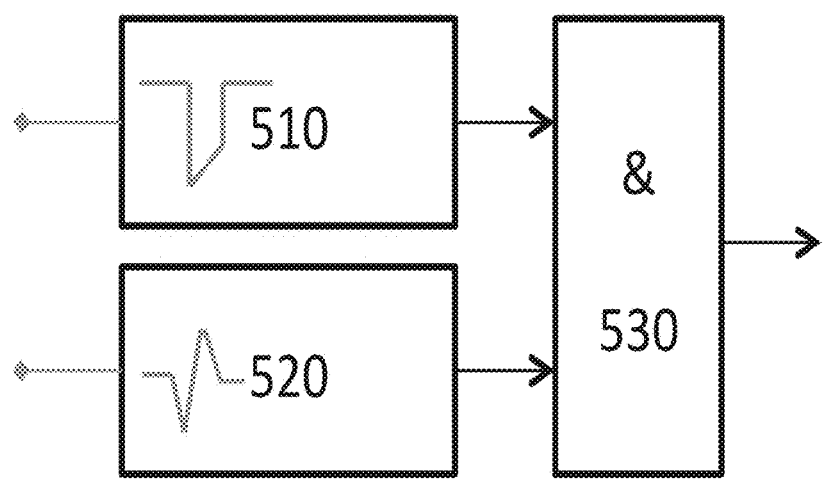
FIG. 5 shows a block diagram for avoiding T-wave over-sensing in the VVT-triggered subcutaneous implantable cardioverter-defibrillator according to one or more embodiments of the present invention.

FIG. 5 shows a block diagram for avoiding T-wave over-sensing in the VVT-triggered subcutaneous implantable cardioverter-defibrillator according to one or more embodiments of the invention. Specifically, sensing units 510 and 520, which are similar to sensing units 210 and 220 in FIG. 1, are logically coupled via an "AND" link 530, depicted as an "&" character in block 530. "AND" link 530 only delivers an R-wave sensing signal when sensing stimulation detection and ECG signal cardiac activity. This allows the subcutaneous implantable cardioverter-defibrillator to discriminate between an R-wave and a T-wave and between an R-wave and noise signals. A valid R-wave detection is only fulfilled in this embodiment, if the subcutaneous implantable cardioverter-defibrillator has detected the combination of an ECG signal in combination with a VVT spike delivered by the pacemaker.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. An implantable cardiac system having an R-spike amplifier comprising:
   an implantable cardiac pacemaker comprising:
      an electrode;
      an electrical signal processor coupled with the electrode, wherein the electrical signal processor is configured to detect a ventricle excitation that is either a sensed ventricular excitation or a stimulated ventricular excitation of a heart; and
      an R-spike amplifier coupled with the electrical signal processor, wherein the R-spike amplifier is configured to amplify the ventricle excitation to create an amplified R-wave or R-spike and output the amplified R-wave and increase an R-wave to T-wave signal to noise ratio associated with the heart.

2. The system according to claim 1, wherein the amplified R-wave is shorter in time duration than the ventricle excitation or longer in the time duration than the ventricle excitation.

3. The system according to claim 1, wherein the amplified R-wave that is output ends before an initial increase in a subsequent T-wave.

4. The system according to claim 1, wherein the implantable cardiac pacemaker is further configured to record a subcutaneous electrocardiogram (ECG) as a time course of electrical activity of the heart,
   wherein the R-spike amplifier is configured to amplify the ventricle excitation during a fraction of time of the time course of the electrical activity of the heart before a subsequent T-wave and output the amplified R-wave.

5. The system according to claim 1, wherein the implantable cardiac pacemaker is a leadless cardiac pacemaker (iLP) configured to be implanted in a ventricle of the heart.

6. The system according to claim 1, wherein the implantable cardiac pacemaker is further configured to deliver a sub-threshold stimulation pulse after the ventricle excitation is sensed.

7. The system according to claim 1, wherein the implantable cardiac pacemaker is further configured to:
   deliver a stimulation pulse after the ventricle excitation is sensed based on a heart rate of the heart, such that:
      when the heart rate is below a first predefined threshold value, the stimulation pulse is delivered as a supra-threshold stimulation pulse; and
      when the heart rate is above a second predefined threshold value, the stimulation pulse is delivered as a sub-threshold stimulation pulse; and
   inhibit delivery of the stimulation pulses after the ventricle excitation is sensed based on the heart rate of the heart, such that:
      when the heart rate lies above the first predefined threshold value and below the second predefined threshold value, the stimulation pulse is not delivered.

8. The system according to claim 1, wherein the implantable cardiac pacemaker further comprises a stimulation electrode and a stimulation unit coupled to the stimulation electrode.

9. The system according to claim 8, wherein the implantable cardiac pacemaker further comprises:
   a sensing unit coupled to the electrode; and
   a control unit coupled to the sensing unit, the stimulation electrode and the electrode.

10. The system according to claim 9, wherein the sensing unit is coupled to the electrical signal processor and is configured to transmit an indication to the control unit that indicates natural ventricular activity of the heart.

11. The system according to claim 10, wherein the implantable cardiac pacemaker further comprises an elevation unit, wherein the elevation unit is controlled by the control unit and is configured to deliver an electrical signal increase that corresponds to an R-wave when the control unit receives the indication that indicates the natural ventricular activity or when a stimulation pulse is delivered via the stimulation unit.

12. The system according to claim 11, wherein the electrical signal increase comprises an increase of the R-wave in electrical activity of the heart to form the amplified R-wave or R-spike.

13. The system according to claim 1, wherein the implantable cardiac pacemaker is operated in a VVT operating mode.

14. The system according to claim 1, further comprising:
a subcutaneous implantable cardioverter-defibrillator communicatively coupled to the implantable cardiac pacemaker, wherein the subcutaneous implantable cardioverter-defibrillator comprises:
- an electrode line that comprises two shock electrode poles, wherein the subcutaneous implantable cardioverter-defibrillator is configured to record a second subcutaneous electrocardiogram (ECG) between the two shock electrode poles;
- a stimulation detection unit coupled with the electrode line wherein the stimulation detection unit is configured to identify and detect a characteristic feature in the subcutaneous electrocardiogram; and
- a sensing unit coupled with the stimulation detection unit wherein the sensing unit is configured to obtain the characteristic feature in the subcutaneous electrocardiogram and sense the amplified R-wave based on the increase in the R-wave to T-wave signal to noise ratio associated with the heart.

15. The system according to claim 14, wherein the electrical signal processor is further configured to amplify a ventricular tachyarrhythmia that is detected, such that the second subcutaneous electrocardiogram further comprises the ventricular tachyarrhythmia as amplified.

16. The system according to claim 14, wherein the implantable cardiac pacemaker further comprises a pacemaker stimulation detection unit coupled to the electrical signal processor, wherein the pacemaker stimulation detection unit is configured to detect a stimulation from the subcutaneous implantable cardioverter-defibrillator and classify the stimulation as effective or ineffective, and wherein the R-spike amplifier is further configured to amplify stimulated ventricle excitation only when the pacemaker stimulation detection unit classifies the stimulation as effective.

17. The system according to claim 14, wherein the implantable cardiac pacemaker further comprises a classification unit configured to detect and classify ventricular tachyarrhythmia from more than one of the ventricle excitations, such that the implantable cardiac pacemaker is further configured to deliver an antitachycardia stimulation when the ventricular tachyarrhythmia is detected, and wherein the subcutaneous implantable cardioverter-defibrillator is further configured to trigger a defibrillation shock when a rate of the antitachycardia stimulation exceeds a predefined ventricular tachyarrhythmia threshold value.

18. The system according to claim 14, wherein the subcutaneous implantable cardioverter-defibrillator further comprises a classification unit configured to detect and classify ventricular tachyarrhythmia or tachycardia and ventricular fibrillation.

19. The system according to claim 14, wherein the sensing unit of the subcutaneous implantable cardioverter-defibrillator is further configured to detect the amplified R-wave and calculate an R-wave to T-wave signal to noise ratio to minimize T-wave over-sensing.

20. The system according to claim 19, wherein the subcutaneous implantable cardioverter-defibrillator is further configured to send a message to the implantable cardiac pacemaker to alter an amplification factor utilized by the R-spike amplifier to create the amplified R-wave based on the R-wave to T-wave signal to noise ratio.

* * * * *